(12) United States Patent
Riehl et al.

(10) Patent No.: US 8,084,441 B2
(45) Date of Patent: *Dec. 27, 2011

(54) CYSTITIS TREATMENT WITH HIGH DOSE CHONDROITIN SULFATE

(75) Inventors: Peter R. Riehl, London (CA); Sungtack Samuel Hahn, Etobicoke (CA)

(73) Assignee: Stellar Pharmaceuticals, Inc., Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/804,478

(22) Filed: Jul. 21, 2010

(65) Prior Publication Data

US 2010/0292182 A1  Nov. 18, 2010

Related U.S. Application Data

(63) Continuation of application No. 10/546,511, filed as application No. PCT/CA2004/000244 on Feb. 18, 2004, now Pat. No. 7,772,210, which is a continuation-in-part of application No. 10/367,970, filed on Feb. 19, 2003, now abandoned.

(51) Int. Cl.
*A61K 31/70* (2006.01)

(52) U.S. Cl. .......................................................... 514/54

(58) Field of Classification Search ...................... 514/54
See application file for complete search history.

(56) References Cited

U.S. PATENT DOCUMENTS

| | | | |
|---|---|---|---|
| 4,840,941 A | 6/1989 | Ueno et al. |
| 4,886,786 A | 12/1989 | Lindstrom et al. |
| 4,943,630 A | 7/1990 | Jacquinet et al. |
| 4,987,222 A | 1/1991 | De Ambrosi et al. |
| 5,008,253 A | 4/1991 | Casu et al. |
| 5,037,810 A | 8/1991 | Saliba, Jr. |
| 5,158,940 A | 10/1992 | LaRocca et al. |
| 5,541,166 A | 7/1996 | Parish et al. |
| 5,605,891 A | 2/1997 | Prino et al. |
| 6,083,933 A | 7/2000 | Hahn |
| 6,143,730 A | 11/2000 | Parish et al. |
| 6,417,173 B1 | 7/2002 | Roufa et al. |
| 6,492,349 B1 | 12/2002 | Henderson |
| 6,537,977 B1 | 3/2003 | Kyogashima et al. |
| 6,689,748 B1 | 2/2004 | Theoharides |
| 6,979,679 B2 | 12/2005 | Marcum |
| 7,485,629 B2 | 2/2009 | Marcum |
| 7,504,387 B2 | 3/2009 | Marcum |
| 7,772,210 B2 | 8/2010 | Riehl et al. |
| 2003/0232100 A1 | 12/2003 | Theoharides |
| 2004/0161476 A1 | 8/2004 | Hahn et al. |
| 2009/0137525 A1 | 5/2009 | Marcum |

FOREIGN PATENT DOCUMENTS

| | | |
|---|---|---|
| CA | 1187798 | 5/1985 |
| CA | 1240929 | 8/1988 |
| CA | 2071898 | 4/1991 |
| CA | 2020199 | 12/1991 |
| CA | 2046037 | 1/1992 |
| CA | 2060223 | 8/1992 |
| CA | 2066785 | 11/1992 |
| CA | 2076063 | 2/1993 |
| CA | 2100657 | 5/1993 |
| CA | 2128160 | 1/1995 |
| CA | 2130295 | 2/1995 |
| CA | 2190107 | 11/1995 |
| CA | 2203621 | 4/1998 |
| CA | 2217134 | 4/1998 |
| CA | 2120367 | 5/2004 |
| EP | 0 636 631 A1 | 2/1995 |
| WO | WO 93/09766 | 5/1993 |
| WO | WO 93/21193 | 10/1993 |
| WO | WO 9400135 | 1/1994 |
| WO | WO 02/09728 A1 | 2/2002 |
| WO | WO 2004/034980 | 4/2004 |
| WO | WO 2004/073584 A2 | 9/2004 |

OTHER PUBLICATIONS

Conte et al., Metabolic Fate of Exogenous Chondroitin Sulfate in Man Arzneim-Forsch./Drug Res. 41(11) 7, 1991, pp. 768-772.
Hurst et al., A Deficit of Chondroitin Sulfate Proteoglycans on the Bladder Uroepithelium in Interstitial Cystitis, Urology, 1996, pp. 817-821, vol. 48.
Hurst et al., A Deficit of Proteoglycans on the Bladder Uroepithelium in Interstitial Cystitis, European Urology Supplements, Official Journal of the European Association of Urology, 2002, pp. 10-13, vol. 2.
Hurst et al., Functional and Structural Characteristics of the Glycosaminoglycans of the Bladder Luminal Lining, J. Urol., 1987, pp. 433-437, vol. 138.
Kurth et al., The Interstitial Cystitis Syndrome: Intravesical and Oral Treatment, European Urology Supplements. 2002, pp. 2-9, vol. 2.
Mast cells may account for success of GAG layer treatments, by editor Norman Bauman, [online][retrieved Jan. 15, 1999]www.ichelp.com.
Medical Device License Homologation d'un Instrument medical.
Parsons et al., The Role of Urinary Potassium in the Pathogenesis and Diagnosis of Interstitial Cystitis, J. Urol., 1998, pp. 1862-1867, vol. 159.
Sant & Larock, Standard Intravesical Therapies for Interstitial Cystitis. In Urologic Clinics of North America, Feb. 1994, pp. 73-83, vol. 21, No. 1.
Schick, Interstitial Cystitis: Diagnosis and Treatment, Journal of CME, Aug. 1998, pp. 55-66. #Sorensen. Chondroitin Sulphate in the Treatment of Interstitial Cystitis and Chronic Inflammatory Disease of the Urinary Bladder, European Urology Supplements, 2002. pp. 14-16, vol. 2.
Steinhoff et al., The efficacy of chondroitin sulfate 0.2% in treating interstitial cystitis, The Canadian Journal of Urology, Feb. 2002, pp. 1454-1458, vol. 9, No. 1.
Steinhoff, The Efficacy of Chrondroitin Sulphate in Treating Interstitial Cystitis, European Urology Supplements, 2002. pp. 14-16. vol. 2.
PCT International Search Report, PCT/CA2004/000244, dated Dec. 13, 2004.

*Primary Examiner* — Elli Peselev
(74) *Attorney, Agent, or Firm* — TraskBritt, P.C.

(57) ABSTRACT

Interstitial cystitis and related GAG-deficient conditions of the bladder and urinary tract are treated by instillation of high dose chondroitin sulfate, such as 400 mg/20 mL. The higher dose of chondroitin is effective for the rapid reduction of symptoms, particularly in patients with severe and otherwise recalcitrant cystitis.

11 Claims, 1 Drawing Sheet

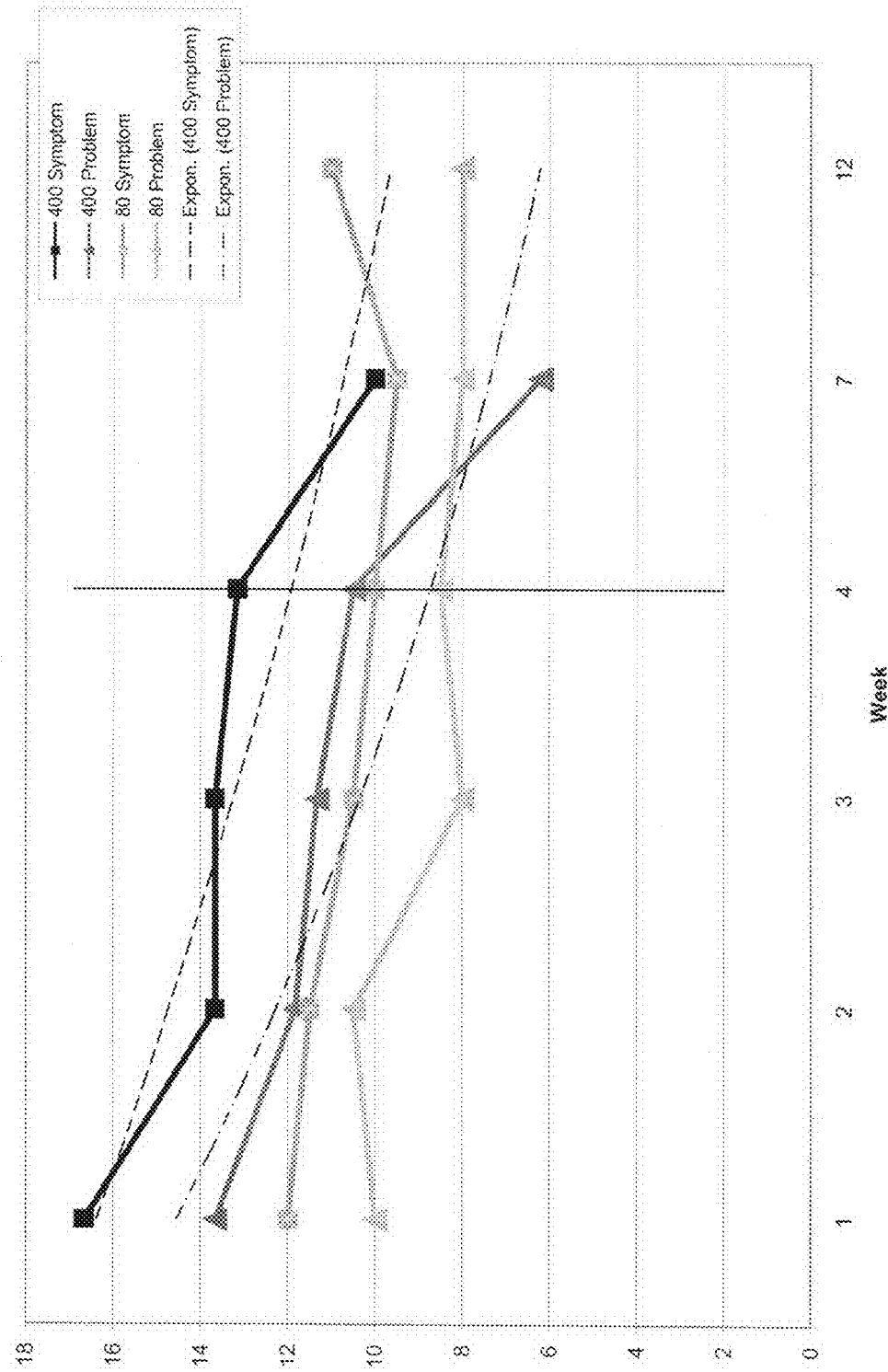

US 8,084,441 B2

CYSTITIS TREATMENT WITH HIGH DOSE CHONDROITIN SULFATE

CROSS-REFERENCE TO RELATED APPLICATIONS

This application is a continuation of U.S. Ser. No. 10/546,511, filed Aug. 18, 2005, now U.S. Pat. No. 7,772,210, issued Aug. 10, 2010, which application is a national phase entry under 35 U.S.C. §371 of PCT International Patent Application PCT/CA2004/000244, filed Feb. 18, 2004, published in English as PCT International Patent Publication WO 2004/073584 A2 on Sep. 2, 2004, which application is a continuation in part of U.S. Ser. No. 10/367,970, filed Feb. 19, 2003, now abandoned, the contents of the entirety of each of which are incorporated herein by this reference.

FIELD OF THE INVENTION

The invention relates to therapeutic agents and methods useful in the treatment of cystitis, including interstitial cystitis, and related bladder conditions.

BACKGROUND

Interstitial cystitis is a bladder condition associated with discomfort and pain elicited by urinary irritants, causing urgency for, and increased frequency of, urination. Because its cause is poorly understood, the development of useful treatments has followed approaches that are largely empirical. These approaches have failed to yield more than a few useful therapeutic agents and treatments. As described by Sant and La Rock in Interstitial Cystitis, Vol. 21 (1), February 1994 at p. 73, current therapies include pharmacotherapy, with intravesical use of dimethyl sulfoxide being the only therapy approved by the FDA. Still, a variety of other agents are in use to treat symptoms of interstitial cystitis, either alone or in combination with DMSO. Such agents include sodium oxychlorosene (Clorpactin), heparin, hyaluronic acid, steroid, sodium bicarbonate, silver nitrate, sodium pentosanpolysulfate, cromolyn sodium, lidocaine and doxorubicin. Many of these agents can be delivered orally, but can be most effective at the GAG surface layer of the urethelium when delivered by instillation either as monotherapy, combination therapy or sequential therapy. These agents and therapies target the bladder mucosal lining, and provide symptomatic relief of pain, frequency and urgency. Of these therapies, however, few offer relief over sustained periods.

More recently, we have described the use of chondroitin sulfate as an instilled preparation for the treatment of interstitial cystitis and related bladder conditions (see, U.S. Pat. No. 6,083,933 and CA 2269260 assigned to Stellar International Inc.). As disclosed in these patents, preparations containing 80 mgs, and up to 200 mgs, of chondroitin sulfate as a 40 mL instillation provided relief from at least one symptom including frequency, pain and urgency, in patients diagnosed with cystitis. In addition, there is described a diagnostic method useful to identify responders to chondroitin sulfate therapy or therapy with other cystitis treatments. In this approach, patient candidates first receive an instilled dose of an irritant such as potassium chloride, and responders are then identified as those patients experiencing relief from the irritant-elicited symptoms upon instillation of the chondroitin sulfate or other therapeutic. For use in such therapy, Stellar International Inc., of London, Ontario, Canada markets the product Uracyst-S™, which is a treatment kit comprising a vial containing 80 mgs of chondroitin sulfate in 40 mL aqueous vehicle (0.2%), and the product Uracyst-S™-Concentrate providing a vial containing 200 mgs of chondroitin in a 10 mL vehicle (2.0%). Results of a study using Uracyst™-S are reported by Steinhoff et al in Can. J. Urol., 2002 Feb. 9(1):1454-58.

SUMMARY OF THE INVENTION

It has now been found that patients suffering from cystitis and related conditions of the bladder and urinary tract respond more rapidly to treatment with chondroitin sulfate when the instilled dose of chondroitin sulfate is increased above 200 mg. It had been assumed that a dose approaching 200 mg was sufficient to saturate the bladder lining and hence deposit, or adsorb, sufficient chondroitin sulfate to protect all available sites of bladder lining erosion. However, it has now surprisingly been found that a more rapid relief from cystitis symptoms can be realized when the instilled dose of chondroitin sulfate is increased, beyond 200 mgs. In addition, it has been found that administration of higher dose chondroitin sulfate provides relief in patients in whom the cystitis is so severe as to be virtually refractory to other conventional forms of cystitis therapy.

Thus, in accordance with one aspect of the invention, there is provided a method for treating a patient afflicted with cystitis or a related condition of the bladder or urinary tract, the method comprising the step of delivering to the patient by instillation a pharmaceutical composition comprising chondroitin sulfate in a unit dose of at least 250 mgs, preferably at least 300 mgs, more preferably at least 350 mgs and most preferably at least 400 mgs. Similarly, the invention provides for the use of chondroitin sulfate in the preparation of a medicament comprising at least 250 mgs of chondroitin sulfate for the treatment of cystitis and related conditions of the bladder or urinary tract.

In other aspects of the invention, there is provided a pharmaceutical composition adapted for delivery to a patient by instillation, the composition comprising chondroitin sulfate at a unit dose of at least 250 mgs, and an aqueous vehicle therefor. In embodiments of the invention, compositions effective to treat cystitis include sterile, aqueous compositions comprising:

(1) a unit dose of highly purified grade chondroitin sulfate of at least 250 mgs, e.g., in the range from 250 mgs to saturation, and (2) a pharmaceutically acceptable aqueous carrier, in a volume that is patient-tolerated and sufficient for exposing the bladder surface area to be treated.

In a particular embodiment of the invention, there is provided a pharmaceutical composition adapted for instillation, the composition comprising chondroitin sulfate in a unit dose of from 250 to 1200 mgs, and from 10 to 100 mL of an aqueous vehicle. In a more specific embodiment, the composition comprises 400 mgs of chondroitin sulfate in 20 mL of an aqueous vehicle, preferably phosphate-buffered saline. In a very specific embodiment, there is provided a sterile chondroitin sulfate solution adapted for instillation, the solution consisting essentially of, and preferably consisting only of, 400 mgs of chondroitin sulfate and 20 mL of an aqueous buffer, preferably phosphate-buffered saline.

BRIEF REFERENCE TO THE DRAWING

FIG. 1 compares, using the Oleary Sant index, results obtained in cystitis patients receiving high dose chondroitin sulfate, with results achieved in patients receiving an 80 mg dose of chondroitin sulfate.

DETAILED DESCRIPTION AND PREFERRED EMBODIMENTS

The compositions and methods of the invention are useful in the treatment and assessment of various forms of cystitis as they occur particularly in the bladder, but also as they occur in the urinary tract including the urethra and those other mucosal surfaces that are exposed to treatment by the vesicular instillation route of administration. By this route, a sterile catheter is placed into the bladder through the urethra, and the treatment solution fed through the catheter. The solution is then held in the bladder for at least 30 minutes or longer before voiding. The forms of cystitis that can be treated include particularly interstitial cystitis and those other forms of cystitis and related bladder conditions that respond to an enhancement of mucosal integrity and barrier function that is believed to result when the present chondroitin sulfate treatment is used. These include radiation-induced cystitis, chemical-induced cystitis, e.g., resulting from chemotherapy and hemorrhagic cystitis, as well as, more generally, GAG-deficient forms of cystitis and GAG-deficiency resulting from chronic urinary tract infection.

Cystitis-related conditions are revealed using an established potassium test, in which a 3.0% KCl solution is instilled into the bladder of the patient candidate. A response to the potassium solution with symptoms characteristic of cystitis indicates GAG deficiency in the bladder lining, suggesting that the patient has either cystitis or a condition related thereto by GAG-deficiency, and identifies the patient as a candidate for chondroitin sulfate therapy.

For use in treating interstitial cystitis and these related conditions, the invention exploits chondroitin sulfate which is an acidic mucopolysaccharide and is one of the glycosaminoglycans (GAGs). Its repeating disaccharide unit is made of glucuronic acid and galactosamine with one sulfate group in a B (1-3') linkage, i.e. N-acetyl galactosamine sulfate. This disaccharide unit is polymerized in B (1-4') linkage.

Chondroitin sulfate (CS) is available in a number of monosulfated forms, varying according to specific chemical composition usually as related to extraction source, chain length usually as related to processing techniques, degree of sulfation, etc. For use in the invention, the CS is desirably in pyrogen free form and is highly purified, thus yielding an "injectable grade" of material having the qualities required for human use by the various regulating agencies. Such material is available from a variety of commercial sources, and the present literature is replete with descriptions of methods suitable for producing such material. In embodiments of the invention, the CS is within the molecular size range of from about 1,000 Daltons to about 75,000 Daltons, for example from about 10,000 Daltons to about 40,000 Daltons. A suitable natural source for CS within this size range is soft connective tissue, such as cartilage. In a specific embodiment, the CS starting material is obtained from either porcine or bovine cartilage and subsequently refined by established methods to yield the desired injectable grade and molecular size fractionated CS. Alternatively, it will be appreciated that the CS can be obtained from other sources, including synthetic routes, or can be blended to combine synthetic and natural CS forms into the desired composition. Desirably, but not essentially, the CS comprises the A-form and C-form of CS, in a blend of form 3:1 to 1:3 on a molar basis, e.g., about 1:1.

It will be understood that the CS typically is in salt form, and in accordance with embodiments of the invention, is in the sodium salt form.

For use, the CS is formulated as a sterile, aqueous solution. The formulation is desirably adapted for single dose administration, although it will be appreciated that a multi-dose formulation may be utilized to treat a number of patients.

In accordance with the invention, the unit dose of CS administered to the patient is at least 250 mgs. More desirably, the unit dose of CS is at least 300 mgs. Preferably, the unit dose is at least 350 mgs. More preferably, the unit dose is at least 400 mgs. The upper end of the acceptable unit dose is capped, in theory, only by the solubility of the given type of CS in the chosen aqueous vehicle, and by the volume of that vehicle used in therapy. At room temperature and in sterile, distilled water, the solubility of CS approaches 50%. Thus, the upper limit of the CS unit dose can be 500 mgs/mL of vehicle. In accordance with the invention, the unit dose of CS is desirably formulated in a solution volume that is sufficient to expose the bladder surface to be treated, and is at least tolerable and more desirably comfortable for the patient. The upper limit for such volumes lies below the volume causing hydrodistention, which is about 250 mL in some patients. For adult patients, solution volumes are suitably from about 5 mL or 10 mL up to about 100 mL, e.g. up to about 75 mL, and preferably up to about 50 mL. In a specific embodiment of the invention, a solution volume of about 40 mL is utilized. Accordingly, the upper limit of the unit dose of CS administrable to the patient at this volume can approach 20,000 mgs.

In embodiments of the invention, the unit dose of CS administered to the patient lies suitably within the range from 250-1,200 mgs, desirably within the range from 300-800 mgs, preferably in the range from 350-600 mgs, and more preferably in the range from 375-500 mgs. In a specific embodiment, the CS is formulated in a unit dose of 400 mgs.

As vehicle for such solutions, there may be employed sterile water, saline or buffered saline. The saline vehicle is particularly useful, and in embodiments of the invention, the vehicle is 0.9% saline. Alternatively, phosphate-buffered saline vehicles may be used. In a specific embodiment, the aqueous vehicle is simply sterile water for injection.

The concentration of CS within the solution will of course vary in accordance with the amount of CS formulated and the solution volume employed. CS is relatively soluble in aqueous vehicles, and a wide range of concentrations may therefore be formulated. In embodiments of the invention, the CS concentration lies within the range from 0.1 mg/mL to 100 mg/mL, preferably 1.0 mg/mL to 50 mg/mL. In a specific embodiment of the invention, the formulation has a CS concentration of about 15-25 mg/mL, e.g., 20 mg/mL. In a particular specific embodiment of the invention, the formulation achieves this concentration by providing a formulation containing 400 mgs of CS in a 20 mL volume of phosphate-buffered saline.

In a specific embodiment of the invention, the sterile chondroin sulfate solution consists of 400 mgs chondroitin sulfate, and 20 mL of aqueous vehicle, such as sterile water, saline or phosphate-buffered saline.

Formulation of the CS will of course be performed in a manner established in the pharmaceutical art. Unit or single doses can be produced simply by metering the unit dose of CS, say 400 mgs, into a vial which then receives 20 mL of vehicle or diluent, under aseptic filling conditions. Alternatively, such a formulation can be prepared by combining commercially available formulations, such as the Uracyst-S-Concentrate, e.g., by combining two 200 mg/10 mL solutions.

In use, the CS composition is administered by instillation or like method that directs the composition to the luminal (mucosal) surface of the affected bladder or associated surface of a patient having the symptoms of cystitis and particularly GAG-deficient cystitis including chemical- and radiation-induced cystitis, hemorrhagic cystitis and, in accordance with a preferred embodiment of the invention, interstitial cystitis. In addition to IC patients, such treatment can be useful, as noted, for "related bladder conditions", i.e., for those patients having an erosion of either the bladder lining or the lining of the urethra or ureters which is sufficiently severe to cause pain or discomfort when chemical irritants are present in the urine. Such related conditions include urinary tract GAG-deficiency resulting from chronic urinary tract infection. With each treatment, the composition is instilled, for instance as a 20 mg/mL dose of CS in a buffer volume of 20 mL, after any residual urine has been removed. The patient then retains the solution for a period desirably of not less than 30 minutes. In a typical treatment regimen, weekly or biweekly treatments are performed for about 6 weeks, and then monthly treatments are performed thereafter until symptoms are relieved. Some patients may benefit from up to 6 weekly instillations, then instillations once monthly or bimonthly thereafter depending on their symptomatic response. Maintenance dosing can be performed using doses of CS that are reduced, e.g., to 200 mgs, if patient symptoms so indicate.

As noted in the examples, patients treated in the manner just described have responded well, by indicating that symptoms of pain, urgency and/or frequency have subsided. The present success with "high dose" chondroitin sulfate is both a surprising and significant result, given, on the one hand, that chondroitin sulfate is both a commercially available and relatively inexpensive agent and, on the other hand, that so few agents tested for IC are found to provide actual benefit to the patient. Patients treated with the high dose chondroitin sulfate responded very rapidly to treatment. Moreover, the success seen in the examples herein provided has been achieved in patients having severe cystitis symptoms who were otherwise refractory to treatment with other available therapies.

It will be appreciated that the present high dose CS therapy can be utilized either as a monotherapy or in combination with other available cystitis treatments. Such known cystitis therapies include those delivered by instillation, such as DMSO, heparin, pentosanpolysulfate and hyaluronic acid. As noted hereinabove, such agents should be administered in a volume sufficient to bathe the bladder lining with an amount of the agent determined to be suitable for investigating a therapeutic effect.

For use in the therapeutic method of the invention, there is further provided by the invention a kit comprising, in combination, (1) a first sterile solution comprising chondroitin sulfate at a unit dose of at least 250 mgs and an aqueous vehicle; and (2) printed instructions teaching the use thereof in accordance with the present treatment method.

Such a kit may take the form of a box or other package in which the sterile solution is provided as a ready-to-use solution, having the concentration and unit dose described hereinabove. The printed instructions will convey to the end-user the methodology of the invention. That methodology is exemplified below.

EXAMPLES

The following describes the treatment of interstitial cystitis patients in a clinical setting.

For use in treatment, chondroitin sulfate, as the sodium salt, was purchased as non-pyrogenic and highly purified grade. The CS was obtained from bovine cartilage to control its purity and composition of chondroitin sulfate in terms of its isomers A/C (60:40) and carboxyl/O-sulfate ratio (about 0.95), with other specifications being the following:

Appearance: white to slightly off-white highly hygroscopic solid powder
Purity (anhydrous basis): >98.0%
pH in 1% water: 5.5-7.5
Specific rotation (4% water): −20 to −30 degrees
Nitrogen (anhydrous basis): 2.5-3.5%
Sulfur (anhydrous basis): 5.0-7.0%
Sulfate ash (anhydrous basis): 21-29%
Heavy metals: <20 ppm
Chloride: <0.1%
Proteins (anhydrous basis): <1.0%
Pyrogen: pyrogen free
Average Molecular Weight: 10,000-40,000 Daltons \

This CS is formulated as a 20.0 mg/mL solution, by blending, the following ingredients:

| Ingredient | Formula Quantity (per mL) |
|---|---|
| Na Chondroitin Sulfate (as anhydrous) | 20.0 mg |
| Sod. Chloride, USP | 8.5 mg |
| Dibasic Sodium Phosphate 7H2O, USP | 0.42 mg |
| Monobasic Sodium Phosphate 2H2O, USP | 0.04 mg |
| Sterile Water for Injection., USP OR Sterile Water for Irrigation USP QS | to Volume |

For compounding, about 20 mL of water for injection, USP, is collected, and the required amount (20 times the amounts noted above per mL of formula to make a 2% solution) of Sodium Chloride is added and mixed until completely dissolved (a minimum of 15 minutes). The required amount of monobasic and dibasic Sodium Phosphate is then added and mixed until completely dissolved (a minimum of 15 minutes). Then, the required amount of Sodium Chondroitin Sulfate, is added and mixed until completely dissolved (a minimum of 4 hours for hydration). If necessary the pH is adjusted to 7.2 0.1 with 1N Sodium Hydroxide in WFI, USP or 1 N Phosphoric Acid in WFI, USP. Then, add sufficient quantity to final volume with sterile water for injection, USP and mix thoroughly. It will be appreciated that this method is also suitable for producing different unit doses of CS, simply by altering the volume of buffer and/or by altering the amount of CS and other noted ingredients. Thus, by this methodology, there are provided such CS formulations as 10-40 mL, e.g., 20 mL, formulations containing 250, 300, 350, 400, 600, 800, 1,000 and 1,200 mgs of CS.

The formulation can further comprise a preservative. In a specific embodiment, the preservative is benzyl alcohol or parabens, e.g., methylparaben, propylparaben and butylparaben and mixtures. For instance, the preservative can be 1.5% w/v benzyl alcohol. In a preferred embodiment, the formulation is adapted as a unit dose, and the preservative is accordingly not essential. Thus, in a specific embodiment, the formulation is essentially free from preservative, and other additives, and consists of aqueous vehicle, e.g. 20 mL, and the chondroitin sulfate, e.g., 400 mgs.

The compounded solution (2% or otherwise) is then sterile filled as 10-40 mL, e.g., 20 mL, aliquots into 50 mL, molded Flint I type vials previously sterilized at 250° C. for 180 minutes, and stoppered using 100% synthetic rubber stoppers of the 20 mm type. The vials are then labeled as sterile sodium chondroitin sulfate solution. Hereinafter, the 400 mg/20 mL formulations, 2.0%, are referred to as "Uracyst-S-400" formulations.

In the alternative, patients received two doses of Uracyst-S-Concentrate (200 mgs/10 mL, purchased from Stellar Healthcare of London, Ontario, Canada) per instillation, to deliver 400 mgs of CS in 20 mL of the buffer.

The CS so formulated (400 mg/20 mL [2.0% w/v], Uracyst-S-400) was assessed, in a pilot study with six patients diagnosed with interstitial cystitis. All patients had positive potassium tests, negative cystoscopies and symptoms of daytime frequency of +8 and/or bladder pain. All patients completed an Oleary Sant questionnaire once a week. The three patients receiving twice weekly treatment completed the Oleary Sant once a week also. The potassium test was performed using the product "Solution K" sold by Stellar Healthcare in London, Ontario, Canada, i.e., by instilling a 3.0% KCl solution in the manner instructed by that supplier.

Patient #1 was referred from another urologist seeking a second opinion regarding a cystectomy. She complained of unremitting and severe bladder pain. She had not found success with any treatment. She received six weekly treatments of intravesical Uracyst-S-400. There was no improvement in her symptom/problem score, and she was referred back to the urologist for cystectomy.

Patient #2 presented with long standing interstitial cystitis (IC) and has had some success with previous treatment. She entered the pilot study due to a prolonged and painful flare-up of her IC. She received intravesical instillations of Uracyst-S-400 on Monday and Thursday for six consecutive weeks. Her symptom and problem score improved each week. She was pain free at week 6.

Patient #3 also presented with long standing IC. She complained of frequent painful flare-ups that include severe frequency and nocturia. The patient was also diagnosed with irritable bowel syndrome (IBS). She was treated with Uracyst-S-400 twice weekly (Mondays and Thursdays) for seven weeks. Although two dosing intervals were missed, the patient's problem and symptom scores each dropped five points by the end of the therapy. The patient continues on Uracyst-S-200 mg therapy q2 weeks and will soon be placed on once monthly instillations at this dose. Her symptoms continue to improve.

Patient #4 was referred for flare-up of IC. She had been on oral treatment for 10 years and experienced frequent flare-ups. She was treated once weekly with Uracyst-S-400 for six weeks. Each of her problem and pain scores decreased/improved by 10 points. The patient continues with monthly instillations of Uracyst-S-200.

Patient #5 was referred for bladder pain and frequency, and presents also with fibromyalgia and osteoarthritis and is on medication for these conditions. She was treated with weekly instillations of Uracyst-S 400 for six consecutive weeks. The symptom score improved by 5 points and the problem score by one point. The treatment improved her bladder pain but did not improve her frequency, so the problem score does not reflect that improvement.

Patient #6 has long standing IC, fibromyalgia, emotional stresses, pelvic pain which may or may not be upregulation from her IC. She is on many medications including morphine for pain. She was initially started on weekly instillations and then switched to twice weekly after the first week. She received Uracyst-S 400 twice weekly for six weeks for a total treatment time of 7 weeks. Although symptom and problem scores were somewhat equivocal owing largely to stresses raised by her other conditions, some improvement was noted. Treatment continues every two weeks with Uracyst-S 200, and will soon be reduced to once monthly dosing.

Thus, six patients with known Interstitial Cystitis were instilled intravesically with Uracyst-S 400 (400 mg in 20 mL phosphate buffer saline) either weekly or twice weekly for 6 weeks. Four of the patients were refractory to other forms of treatment, one patient was in a flare-up while on Elmiron®, and one was new to treatment. Three of the four refractory patients were instilled twice weekly with URACYST-S 400 mg. There were no side affects that could be associated with the instillation of the solution. One patient complained of feeling worse after the first instillation but did not want to stop the treatment-after switching to a self-lubricating catheter; there were no further complaints of feeling worse. One patient stated she had a 10 minute total body flush one hour post instillation on the first two instillations; this did not occur on subsequent instillations. There appears to be a shorter time to improvement with the 400 mg Uracyst-S has thus demonstrated that it provides faster relief of problems and symptoms of IC patients. Three of the refractory patients had mild to significant improvement. The two non refractory patients showed improvement in the six weeks of instillation.

The improvements in voiding and pain seen in this patient population are graphed in FIG. 1, according to scores recorded using the Oleary Sant scoring system established for interstitial cystitis. It will be noted, as a trend, that this patient population reported overall significant improvement in symptoms over the noted course of therapy ("400 Symptom, 400 Problem"). For comparison, FIG. 1 also shows the improvement in symptom scores in a patient population, albeit a different interstitial cystitis patient population, treated with chondroitin sulphate formulated at 80 mgs/40 mL ("80 Symptom, 80 Problem"). As shown, the 400 mg dosing therapy provided significant improvement in patients with symptoms and problems more severe than those treated with at the 80 mg dose. The 400 mg population, for instance, scored above 12 in both categories assessed, compared with a score of 12 or less in the 80 mg population. Moreover, the rate at which those symptoms were improved using the 400 mg dose was far more rapid than in patients receiving the 80 mg dose.

It will thus be appreciated that high dose chondroitin sulfate provides a therapy useful in the treatment of patients suffering from cystitis, and is particularly useful for the treatment of patients presenting with severe or long-term interstitial cystitis and related forms of GAG-deficient cystitis.

What is claimed is:

1. A method of treating cystitis in a subject in need thereof, the method comprising:
   treating the subject with a pharmaceutical composition comprising:
   a unit dose of chondroitin sulfate in an amount of at least 350 mg, and
   an aqueous vehicle in a volume of from 10 mL to 100 mL,
   wherein the pharmaceutical composition is adapted for instillation to the bladder of the subject, so as to treat the cystitis in the subject.

2. The method according to claim 1, wherein the chondroitin sulfate is present in an amount of 400 mg.

3. The method according to claim 1, wherein the aqueous vehicle is present in an amount of 20 mL.

4. The method according to claim 1, wherein the aqueous vehicle is phosphate-buffered saline.

5. The method according to claim 1, wherein the cystitis is interstitial cystitis.

6. The method according to claim 1, wherein treating cystitis with the pharmaceutical composition comprises:
   providing a subject afflicted with cystitis or a related condition in which one or more cystitis symptoms are elicited in the subject afflicted upon instillation of a potassium chloride solution; and
   instilling the pharmaceutical composition into the bladder or urinary tract of the subject.

7. The method according to claim 6, wherein the instilling is performed at least once weekly for a period of at least 6 weeks.

8. The method according to claim 6, wherein the instilling is performed at least twice weekly for a period of at least 6 weeks.

9. The method according to claim 1, wherein the unit dose of chondroitin sulfate is at most equivalent to the solubility of chondroitin sulfate is said vehicle.

10. The method according to claim 1, wherein the unit dose of chondroitin sulfate is less than or equal to 1200 mg.

11. The method according to claim 1, wherein the unit dose of chondroitin sulfate is less than or equal to 800 mg.

* * * * *